United States Patent
Kojima et al.

(10) Patent No.: US 11,419,854 B2
(45) Date of Patent: Aug. 23, 2022

(54) MEDICAMENT CONTAINING PEMAFIBRATE

(71) Applicant: KOWA COMPANY, LTD., Nagoya (JP)

(72) Inventors: Satoshi Kojima, Chuo-ku (JP); Ryohei Tanigawa, Chuo-ku (JP)

(73) Assignee: KOWA COMPANY, LTD., Nagoya (JP)

( * ) Notice: Subject to any disclaimer, the term of this patent is extended or adjusted under 35 U.S.C. 154(b) by 0 days.

(21) Appl. No.: 16/609,249

(22) PCT Filed: Jun. 29, 2018

(86) PCT No.: PCT/JP2018/024953
§ 371 (c)(1),
(2) Date: Oct. 29, 2019

(87) PCT Pub. No.: WO2019/004465
PCT Pub. Date: Jan. 3, 2019

(65) Prior Publication Data
US 2020/0046686 A1 Feb. 13, 2020

(30) Foreign Application Priority Data
Jun. 30, 2017 (JP) .............................. JP2017-128181

(51) Int. Cl.
| | | |
|---|---|---|
| *A61K 31/423* | (2006.01) | |
| *A61P 1/16* | (2006.01) | |
| *A61P 3/06* | (2006.01) | |
| *A61P 3/10* | (2006.01) | |
| *A61P 9/00* | (2006.01) | |
| *A61P 9/10* | (2006.01) | |
| *A61P 43/00* | (2006.01) | |

(52) U.S. Cl.
CPC .............. *A61K 31/423* (2013.01); *A61P 1/16* (2018.01)

(58) Field of Classification Search
CPC . A61K 31/423; A61P 1/16; A61P 3/00; A61P 3/06; A61P 3/10; A61P 9/00; A61P 9/10; A61P 29/00; A61P 43/00
See application file for complete search history.

(56) References Cited

U.S. PATENT DOCUMENTS

| | | | |
|---|---|---|---|
| 2005/0101636 A1 | 5/2005 | Yamazaki et al. | |
| 2006/0189667 A1 | 8/2006 | Yamazaki et al. | |

FOREIGN PATENT DOCUMENTS

| | | |
|---|---|---|
| CN | 104640544 A | 5/2015 |
| CN | 105307652 A | 2/2016 |
| WO | WO 2005/023777 A1 | 3/2005 |

OTHER PUBLICATIONS

Rinella, M. E., "Nonalcoholic fatty liver disease: a systematic review." Jama 313.22 (2015): 2263-2273.*
Tan, H.-H. and Schiano, T.D., "Effects of liver disease on drug metabolism in humans." Encyclopedia of Drug Metabolism and Interactions (2011): 1-46.*
International Search Report dated Sep. 11, 2018 in PCT/JP2018/024953 filed on Jun. 29, 2018.
Ishibashi, S. et al., "Effects of K-877, a novel selective PPARα modulator (SPPARMα), in dyslipidaemic patients: A randomized, double blind, active- and placebo-controlled, phase 2 trial," ELSEVIER, Atherosclerosis, vol. 249, Jun. 2016, pp. 36-43.
Hosford, D. et al., "Dose Adjustment Should Be Considered for the Administration of Pemafibrate in Patients with Impaired Hepatic Function," Abstracts / Atherosclerosis Supplements, vol. 32, Jun. 2018, p. 150 (total 2 pages).
Tanaka, T. et al., "The Influence of Pemafibrate (Parmodia® Tablet) on Liver and Renal Function," Japanese Pharmacology & Therapeutics, Vo. 45, No. 11, Nov. 2017, pp. 1775-1785 (total 14 pages).
"Lipidil (registered trademark) Tablets" package insert, revised in Feb. 2017 (6th edition), with computer generated Partial English translation (total 5 pages).
"Bezatol (registered trademark) SR Tablets" package insert, revised in Jan. 2017 (14th edition), with computer generated Partial English translation (total 5 pages).
"Medical Viewpoint", vol. 36, No. 10, Oct. 10, 2015, with computer generated Partial English translation (total 11 pages).
Extended European Search Report dated Feb. 17, 2021 in corresponding European Patent Application No. 18823485.0 citing document AX therein, 7 pages.
Anonimous: "Report on the Deliberation Results", Jun. 13, 2017, XP55771515, 71 page, Retrieved from the Internet: URL:https:www.pmda.go.jp/files/000226672.pdf [retrieved on Feb. 2, 2021].
Chinese Office Action dated May 31, 2022 in corresponding Chinese Patent Application No. 201880043945.8, (with English Machine Translation).

* cited by examiner

*Primary Examiner* — John M Mauro
(74) *Attorney, Agent, or Firm* — Oblon, McClelland, Maier & Neustadt, L.L.P.

(57) ABSTRACT

To provide an appropriate method of treatment with pemafibrate for a liver cirrhosis patient.
The present invention relates to the use of pemafibrate in a liver cirrhosis patient.
More particularly, the present invention relates to a regimen for administering a reduced dose of pemafibrate to a liver cirrhosis patient in need of treatment with pemafibrate than to persons with normal liver function.

8 Claims, No Drawings

MEDICAMENT CONTAINING PEMAFIBRATE

TECHNICAL FIELD

The present invention relates to a pharmaceutical kit containing pemafibrate.

BACKGROUND ART

Pemafibrate (Chemical name: (2R)-2-[3-({1,3-benzoxazol-2-yl[3-(4-methoxyphenoxy)propyl]amino}m ethyl)phenoxy]butanoic acid), a salt thereof, or a solvate of any of these are known as PPARα-activating compounds and to be useful in the prevention and/or treatment of diseases such as dyslipidemia (Patent Literature 1).

As other compounds activating PPARα, for example, fenofibrate and bezafibrate are known, and these compounds are widely used as a pharmaceutical drug. Although it has been reported that fenofibrate is excreted through kidneys, fenofibrate may aggravate hepatic impairment, and therefore, fenofibrate is contraindicated in patients with hepatic impairment. Moreover, since fenofibrate is liable to cause abnormal changes in liver function tests, it is necessary to cautiously administer fenofibrate to patients who showed disorder in liver function tests or to patients with a history of hepatic impairment (Non-Patent Literature 1). Bezafibrate is excreted in the urine primarily via kidneys. Since its blood level may increase, bezafibrate should be administered with caution to patients with hepatic disorder or a history of hepatic disorder (Non-Patent Literature 2). Meanwhile, as reported in Non-Patent Literature 3, pemafibrate, unlike fenofibrate and bezafibrate, is rarely excreted via kidneys. Therefore, pemafibrate is expected to be an effective and safe therapeutic agent for a patient with renal impairment. However, no specific metabolic pathway or route of excretion has been established, nor has it been described or suggested to what extent pemafibrate increases exposure when pemafibrate is administered to a patient with hepatic impairment.

PRIOR ART DOCUMENTS

Patent Literature

[Patent Literature 1] WO2005/023777 pamphlet

Non-Patent Literature

[Non-Patent Literature 1] "Lipidil (registered trademark) Tablets" package insert, revised in February 2017 (6th edition)
[Non-Patent Literature 2] "Bezatol (registered trademark) SR Tablets" package insert, revised in January 2017 (14th edition)
[Non-Patent Literature 3] Medical Viewpoint Vol. 36 No. 10, Oct. 10, 2015

SUMMARY OF THE INVENTION

Problem to be Solved by the Invention

An objective of the present invention is to provide an appropriate therapeutic method for a liver cirrhosis patient with pemafibrate.

Means for Solving the Problem

In order to achieve the above objectives, the present inventors studied extensively. The present inventors have found that, although pemafibrate differs from fenofibrate and bezafibrate in the metabolic and excretional routes, when pemafibrate was administered to patients with hepatic impairment, increased exposure to pemafibrate was observed in liver cirrhosis patients whereas no remarkable increase in exposure to pemafibrate was observed in fatty liver patients compared to persons with normal liver function, and that it is better to reduce the dose of pemafibrate in order to effectively and safely treat them with pemafibrate. Thereby the present inventors have completed the present invention.

The present invention provides the following [1] to [37].
[1] A pharmaceutical kit for treating a patient in need of treatment with pemafibrate, comprising a medicament comprising pemafibrate, a salt thereof, or a solvate of any of these, and an instruction describing reduction of the dose of the medicament when the patient is a liver cirrhosis patient.
[2] The pharmaceutical kit according to [1], wherein the treatment with pemafibrate is treatment of one or more diseases selected from the group consisting of hyperlipidemia, dyslipidemia, arteriosclerosis, diabetes mellitus, diabetic complications, inflammation, non-alcoholic steatohepatitis, primary biliary cirrhosis and heart disease.
[3] The pharmaceutical kit according to [1] or [2], wherein the medicament comprising pemafibrate, a salt thereof, or a solvate of any of these is a medicament comprising pemafibrate.
[4] The pharmaceutical kit according to any one of [1] to [3], comprising an instruction describing reduction of the dose of the medicament to ½ or less of the dose for a person with normal liver function, when the patient is a mild liver cirrhosis patient.
[5] The pharmaceutical kit according to any one of [1] to [3], comprising an instruction describing administration of the medicament as 0.1 mg to 0.2 mg of pemafibrate per day, when the patient is a mild liver cirrhosis patient.
[6] The pharmaceutical kit according to any one of [1] to [3], comprising an instruction describing administration of the medicament as 0.05 mg of pemafibrate twice per day, when the patient is a mild liver cirrhosis patient.
[7] The pharmaceutical kit according to any one of [1] to [3], comprising an instruction describing administration of the medicament as 0.1 mg of pemafibrate twice per day, when the patient is a mild liver cirrhosis patient.
[8] The pharmaceutical kit according to any one of [1] to [3], comprising an instruction describing reduction of the dose of the medicament to ¼ or less of the dose for a person with normal liver function, when the patient is a moderate liver cirrhosis patient.
[9] The pharmaceutical kit according to any one of [1] to [3], comprising an instruction describing administration of the medicament as 0.05 mg to 0.1 mg of pemafibrate per day, when the patient is a moderate liver cirrhosis patient.
[10] The pharmaceutical kit according to any one of [1] to [3], comprising an instruction describing administration of the medicament as 0.025 mg of pemafibrate twice per day, when the patient is a moderate liver cirrhosis patient.
[11] The pharmaceutical kit according to any one of [1] to [3], comprising an instruction describing administration of the medicament as 0.05 mg of pemafibrate twice per day, when the patient is a moderate liver cirrhosis patient.
[12] A pharmaceutical kit for treating a patient in need of treatment with pemafibrate, comprising a medicament comprising pemafibrate, a salt thereof, or a solvate of any of these, and an instruction to consider reducing the dose of the medicament if necessary, when the patient is a liver cirrhosis patient.

[13] The pharmaceutical kit according to [12], wherein the treatment with pemafibrate is treatment of one or more diseases selected from the group consisting of hyperlipidemia, dyslipidemia, arteriosclerosis, diabetes mellitus, diabetic complications, inflammation, non-alcoholic steatohepatitis, primary biliary cirrhosis and heart disease.

[14] The pharmaceutical kit according to [12] or [13], wherein the medicament comprising pemafibrate, a salt thereof, or a solvate of any of these is a medicament comprising pemafibrate.

[15] The pharmaceutical kit according to any one of [12] to [14], comprising an instruction to consider reducing the dose of the medicament if necessary, when the patient is a mild liver cirrhosis patient.

[16] A medicament for the treatment of a liver cirrhosis patient in need of treatment with pemafibrate, comprising pemafibrate, a salt thereof, or a solvate of any of these, for administering at a dose lower than the dose for a person with normal liver function.

[17] The medicament according to [16], wherein the treatment with pemafibrate is treatment of one or more diseases selected from the group consisting of hyperlipidemia, dyslipidemia, arteriosclerosis, diabetes mellitus, diabetic complications, inflammation, non-alcoholic steatohepatitis, primary biliary cirrhosis and heart disease.

[18] The medicament according to [16] or [17], comprising pemafibrate.

[19] The medicament according to any one of [16] to [18], for administering to a mild liver cirrhosis patient at a dose of ½ or less of the dose for a person with normal liver function.

[20] The medicament according to any one of [16] to [18], for administering 0.1 mg to 0.2 mg of pemafibrate per day to a mild liver cirrhosis patient.

[21] The medicament according to any one of [16] to [18], for administering 0.05 mg of pemafibrate twice per day to a mild liver cirrhosis patient.

[22] The medicament according to any one of [16] to [18], for administering 0.1 mg of pemafibrate twice per day to a mild liver cirrhosis patient.

[23] The medicament according to any one of [16] to [18], for administering to a moderate liver cirrhosis patient at a dose of ¼ or less of the dose for a person with normal liver function.

[24] The medicament according to any one of [16] to [18], for administering 0.05 mg to 0.1 mg of pemafibrate per day to a moderate liver cirrhosis patient.

[25] The medicament according to any one of [16] to [18], for administering 0.025 mg of pemafibrate twice per day to a moderate liver cirrhosis patient.

[26] The medicament according to any one of [16] to [18], for administering 0.05 mg of pemafibrate twice per day to a moderate liver cirrhosis patient.

[27] A method of treating a liver cirrhosis patient with pemafibrate, comprising administering a medicament comprising pemafibrate, a salt thereof, or a solvate of any of these at a dose lower than the dose for a person with normal liver function.

[28] The method according to [27], for treating one or more diseases selected from the group consisting of hyperlipemia, dyslipidemia, dyslipidemia, arterial sclerosis, diabetes mellitus, diabetic complications, inflammation, non-alcoholic steatohritis, primary biliary circulation and heart disease.

[29] The method according to [27] or [28], wherein the medicament comprising pemafibrate, a salt thereof, or a solvate of any of these is a medicament comprising pemafibrate.

[30] The method according to any one of [27] to [29], comprising administering the medicament to a mild liver cirrhosis patient at a dose of ½ or less of the dose for a person with normal liver function.

[31] The method according to any one of [27] to [29], comprising administering the medicament as 0.1 mg to 0.2 mg of pemafibrate per day to a mild liver cirrhosis patient.

[32] The method according to any one of [27] to [29], comprising administering the medicament as 0.05 mg of pemafibrate twice per day to a mild liver cirrhosis patient.

[33] The method according to any one of [27] to [29], comprising administering the medicament as 0.1 mg of pemafibrate twice per day to a mild liver cirrhosis patient.

[34] The method according to any one of [27] to [29], comprising administering the medicament to a moderate liver cirrhosis patient at a dose of ¼ or less of the dose for a person with normal liver function.

[35] The method according to any one of [27] to [29], comprising administering the medicament as 0.05 mg to 0.1 mg of pemafibrate per day to a moderate liver cirrhosis patient.

[36] The method according to any one of [27] to [29], comprising administering the medicament as 0.025 mg of pemafibrate twice per day to a moderate liver cirrhosis patient.

[37] The method according to any one of [27] to [29], comprising administering the medicament as 0.05 mg of pemafibrate twice per day to a moderate liver cirrhosis patient.

Effect of the Invention

The present invention enables therapeutic treatment for a liver cirrhosis patient with pemafibrate effectively and safely by controlling the drug exposure.

DETAILED DESCRIPTION OF THE INVENTION

In a first embodiment, the present invention provides a pharmaceutical kit for treating a patient in need of treatment with pemafibrate, comprising a medicament comprising pemafibrate, a salt thereof, or a solvate of any of these, and an instruction describing reduction of the dose of the medicament when the patient is a liver cirrhosis patient.

In a second embodiment, the present invention provides a pharmaceutical kit for treating a patient in need of treatment with pemafibrate, comprising a medicament comprising pemafibrate, a salt thereof, or a solvate of any of these, and an instruction to consider reducing the dose of the medicament if necessary, when the patient is a liver cirrhosis patient.

In a third embodiment, the present invention provides a medicament for the treatment of a liver cirrhosis patient in need of treatment with pemafibrate, comprising pemafibrate, a salt thereof, or a solvate of any of these, for administering at a dose lower than the dose for a person with normal liver function.

In a fourth embodiment, the present invention provides a method of treating a liver cirrhosis patient with pemafibrate, comprising administering a medicament comprising pemafibrate, a salt thereof, or a solvate of any of these at a dose lower than the dose for a person with normal liver function.

In the present invention, pemafibrate represents (2R)-2-[3-({1,3-benzoxazol-2-yl[3-(4-methoxyphenoxy)propyl]amino}methyl)phenoxy]butanoic acid, represented by the following formula (A).

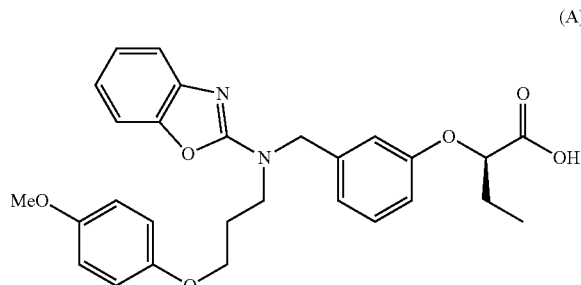

(A)

The compounds can be prepared, for example, according to the methods described in Patent Literature 1.

In one embodiment of the present invention, a salt or a solvate of pemafibrate can also be used. The salt and solvate of pemafibrate can be prepared by conventional methods. The salt of pemafibrate is not particularly limited as long as it is pharmaceutically acceptable, and examples thereof include alkali metal salts such as sodium salts and potassium salts; alkaline earth metal salts such as calcium salts and magnesium salts; organic base salts such as ammonium salts and trialkylamine salts; mineral acid salts such as hydrochloride salts and sulfate salts; and organic acid salts such as acetate salts. The solvate of pemafibrate or its salt includes a hydrate, an alcoholate, such as an ethanolate.

In one embodiment of the present invention, the medicament comprising pemafibrate, a salt thereof, or a solvate of any of these may be in the form of a tablet, a capsule, a granule, a powder, a lotion, an ointment, an injection, a suppository, and the like, using other pharmaceutically acceptable carriers. These preparations can be produced by known methods. In one embodiment of the present invention, the medicament comprising pemafibrate, a salt thereof, or a solvate of any of these may be administered by an oral or parenteral administration, and an oral administration is preferable.

As used herein, "a patient in need of treatment with pemafibrate" represents a patient suffering from one or more diseases in which symptoms may disappear or be alleviated by administration of pemafibrate, a salt thereof, or a solvate of any of these. Such diseases include, but are not limited to, one or more selected from hyperlipidemia, dyslipidemia, arteriosclerosis, diabetes mellitus, diabetic complications, inflammation, non-alcoholic steatohepatitis, primary biliary cirrhosis and heart disease.

Liver cirrhosis is a change based on long-term injury of liver tissues, and portal hypertension, ascites, hepatic encephalopathy, pulmonary disorder, cardiac disorder, renal disorder, serum sodium lowering, etc. are observed due to decrease of liver parenchymal cells, blood flow disturbance by liver fibrosis and structural remodeling, portal-large circulation shunt formation, etc. In the present specification, "mild liver cirrhosis" refers to liver cirrhosis that exhibits a degree of liver damage classified as "A" according to the Child Pugh classification, and "moderate liver cirrhosis" refers to liver cirrhosis that exhibits a degree of liver damage classified as "B" according to the Child-Pugh classification. Here, the Child-Pugh classification is a method of classifying the severity of liver disorder by adding the points of each item shown in Table 1 and by the total points, and is judged as "A (mild)" when the total points are 5 to 6 points, "B (moderate)" when the total points are 7 to 9 points, and "C (severe)" when the total points are 10 to 15 points.

TABLE 1

Child-Pugh Classification Point Score Table

| Symptoms and Test Values | Point | | |
|---|---|---|---|
| | 1 | 2 | 3 |
| Encephalopathy* | None | 1 or 2 | 3 or 4 |
| Ascites | None | Slight | Moderate |
| Serum-bilirubin (mg/dL) | <2 | 2 to 3 | >3 |
| Serum albumin (g/dL) | >3.5 | 2.8 to 3.5 | <2.8 |
| Prothrombin activity (%) | 70< | 40~70 | <40 |

*Encephalopathy is assessed on the following scale

| Grade | |
|---|---|
| 0 | Normal consciousness, personality, neurologic examination, and brain waves |
| 1 | Uncomfortable, sleep disturbances, anger/excitement, tremors, handwriting disturbances, 5 cps waves |
| 2 | Lethargy, disorientation of time, inappropriate behavior, asterixis, ataxia, and mild triphasic wave |
| 3 | Sleepiness, confusion, disorientation of place, hyperreflexia, rigidity, slow waves |
| 4 | Coma, refractoriness, brain removal, and mild 2-3 cps delta activity |

Those skilled in the art will be able to diagnose whether a patient is cirrhotic or not by combining physical findings, blood chemistry findings, scoring systems combining multiple blood chemistry findings, diagnostic imaging including elastography, laparoscopic naked eye findings, and liver biopsy tissue findings, as appropriate.

Those skilled in the art can also determine the severity of a patient's liver disorder according to the Child-Pugh classification described above.

In this specification, "instruction" refers to an instruction for physicians, dentists, pharmacists, and/or patients regarding the use of a medicament, e.g., an instruction describing the dose and administration, pharmacology, pharmacokinetics, adverse effects, precautions for use of the medicament.

Examples of the instruction include, but are not limited to, package inserts (package insert or product labeling), interview forms, product information (Product Information), prescription information (Prescribing Information), etc. In one embodiment of the present invention, the instruction is preferably a package insert.

In the present invention, "reduction of the dose of the medicament" refers to reducing the dose of the medicament for a person with normal liver function, and "dose" means the amount of active ingredient as pemafibrate administered on a daily basis or a one time basis.

In one embodiment of the present invention, when treatment with pemafibrate is performed on a liver cirrhosis patient, the dose may be reduced to ¾ or less, ⅔ or less, ½ or less, ⅓ or less, or ¼ or less of the dose for a person with normal liver function.

In one embodiment of the present invention, when a liver cirrhosis patient is treated with pemafibrate, the dose may be reduced to 0.9-fold, 0.8-fold, 0.75-fold, 0.7-fold, 0.6-fold, 0.5-fold, 0.4-fold, 0.3-fold, 0.25-fold, 0.2-fold, or 0.1-fold the dose for a person with normal liver function.

For example, in order to reduce the dose to ½ of the dose for a person with normal liver function, if the therapeutic effect is obtained by administering 0.1 mg to 0.2 mg twice per day to a person with normal liver function, 0.05 mg to 0.1 mg twice per day to a person with liver cirrhosis may be administered, and if the therapeutic effect is obtained by administering 0.2 mg to 0.4 mg once per day to a person with normal liver function, 0.1 mg to 0.2 mg once per day to a person with liver cirrhosis may be administered.

Similarly, for example, in order to reduce the dose to ¼ of the dose for a person with normal liver function, if the therapeutic effect is obtained by administering 0.1 mg to 0.2 mg twice per day to a person with normal liver function, 0.025 mg to 0.05 mg twice per day to a person with liver cirrhosis may be administered, and if the therapeutic effect is obtained by administering 0.2 mg to 0.4 mg once per day to a person with normal liver function, 0.05 mg to 0.1 mg per day may be administered to a person with liver cirrhosis.

In one embodiment of the present invention, when treatment with pemafibrate is performed on a Child-Pugh Class A liver cirrhosis patient (a patient with mild liver cirrhosis), pemafibrate is administered at a dose reduced to ½ or less of the dose when administered to a person with normal liver function. For example, if the therapeutic effect is achieved by administering 0.1 mg to 0.2 mg of pemafibrate twice per day to a person with normal liver function, 0.05 mg to 0.1 mg twice per day may be administered to a patient with Child-Pugh class A liver cirrhosis. When a therapeutic effect is observed in a person with normal liver function by administering 0.2 mg to 0.4 mg of pemafibrate per day, 0.05 mg to 0.1 mg of pemafibrate per day may be administered to a patient with Child-Pugh class A liver cirrhosis.

In one embodiment of the present invention, when treatment with pemafibrate is performed on a Child-Pugh Class B cirrhotic patient (a moderate cirrhotic patient), pemafibrate is administered at a dose reduced to ¼ or less of the dose when administered to a person with normal liver function. For example, if the therapeutic effect is achieved by administering 0.1 mg to 0.2 mg of pemafibrate twice per day to a person with normal liver function, 0.025 mg to 0.05 mg of pemafibrate twice per day may be administered to a Child-Pugh class B liver cirrhosis patient. When a therapeutic effect is observed in a person with normal liver function by administering 0.2 mg to 0.4 mg of pemafibrate per day, 0.05 mg to 0.1 mg of pemafibrate per day may be administered to a patient with Child-Pugh class B liver cirrhosis.

The present invention will be described hereafter in more detail by way of examples, which do not limit the present invention.

EXAMPLES

Example 1: Pharmacokinetic Study of Pemafibrate in Liver Cirrhosis Patients

To investigate the effect of liver cirrhosis on the pharmacokinetics of pemafibrate, a clinical study was conducted on mild liver cirrhosis patients, moderate liver cirrhosis patients, fatty liver patients, and persons with normal liver function.

1. Subject

Subjects were classified into four groups according to the criteria in Table 2. As a result, the subjects included 8 mild liver cirrhosis patients, 6 moderate liver cirrhosis, patients, 10 fatty liver patients, and 8 persons with normal liver function.

TABLE 2

| Subject | |
|---|---|
| Criteria | |
| Group of mild liver cirrhosi patients | Diagnosed with liver cirrhosis and classified as Child Pugh Class A |
| Group of moderate liver cirrhosis patients | Diagnosed with liver cirrhosis and classified as Child-Pugh Classification B |
| Group of fatty liver patients | ALTs of 45 IU/L or more and diagnosed fatty liver by various imaging tests such as abdominal ultrasonography |
| Group of persons with normal liver function | No complication of liver disease; AST, ALT, γ-GTP, and ALP were all within the standard value; and Total bilirubin was within the standard value, or total bilirubin was outside the standard value, and the physician judged as constitutive jaundice, but no abnormality was observed by various imaging tests such as abdominal ultrasonography |

2. Test Method (1) Administration and Measurement Subjects received a single oral dose of 0.2 mg of study drug (pemafibrate) in the fasting state (fasting for at least 10 hours).

Blood samples were collected at a total of 16 time points immediately before administration of the investigational product and 0.25, 0.5, 1, 1.5, 2, 3, 4, 6, 8, 10, 12, 16, 24, 36, and 48 hours after administration of the investigational product, and plasma concentrations of unchanged pemafibrate were measured by high performance liquid chromatography/tandem mass spectrometry (High-Performance Liquid Chromatography/Tandem Mass Spectrometry: LC-MS-MS method).

(2) Analysis

To investigate the pharmacokinetics, the pharmacokinetic parameters (maximum concentration ($C_{max}$) and area under the concentration-time curves to infinity ($AUC_{0-t}$) of unchanged pemafibrate were evaluated by calculating the ratio of the geometric mean values of the groups of patients with hepatic dysfunction to those with normal hepatic function and their 90% confidence intervals.

3. Results

The ratios of each group of patients with hepatic dysfunction to the group with normal hepatic function for each of $C_{max}$ and $AUC_{0-t}$ of unchanged pemafibrate are shown in Table 3.

TABLE 3

$C_{max}$ of patients with fatty liver and liver cirrhosis compared with persons with normal liver function (n = 8) and Geometric mean of the $AUC_{0-t}$ [90% confidence interval]

| | $C_{max}$ | $AUC_{0-t}$ |
|---|---|---|
| Group of patients with fatty liver (n = 10) | 1.198 [0.819, 1.750] | 1.194 [0.836, 1.707] |
| Group of patients with mild liver cirrhosis Child-Pugh class A (n = 8) | 2.329 [1.561, 3.475] | 2.076 [1.425, 3.026] |
| Patients with moderate liver cirrhosis Child-Pugh class B (n = 6) | 3.882 [2.520, 5.980] | 4.191 [2.790, 6.294] |

Regarding geometric mean values of $C_{max}$ and $AUC_{0-t}$, the ratio of liver cirrhosis patients to persons with normal liver function was approximately 2-fold for mild liver cirrhosis patients (Child-Pugh Class A) and approximately 4-fold for moderate liver cirrhosis patients (Child-Pugh Class B). The fatty liver patient group showed about 1.2 times the geometric mean values compared with the liver function normal patient group. Compared with persons with normal liver function, $C_{max}$ and $AUC_{0-t}$ were slightly higher in fatty liver patients, but not clinically significant, and increased exposure was observed in liver cirrhosis patients. From the above, it was conceived that it is necessary to adjust the dose of pemafibrate for liver cirrhosis patients, such as by reducing the dose to ½ when administering pemafibrate to mild liver cirrhosis patients and by reducing the dose to ¼ when administering pemafibrate to moderate liver cirrhosis patients.

INDUSTRIAL APPLICABILITY

According to the present invention, methods of treatment that are balanced in efficacy and safety, with pemafibrate can be provided for a liver cirrhosis patient.

The invention claimed is:

1. A method of treating a liver cirrhosis patient with pemafibrate, comprising administering a medicament comprising pemafibrate, a salt thereof, or a solvate thereof as:
   (i) 0.1 mg to 0.2 mg of pemafibrate per day to a mild liver cirrhosis patient, or
   (ii) 0.05 mg to 0.1 mg of pemafibrate per day to a moderate liver cirrhosis patient.

2. The method according to claim 1, for treating at least one disease selected from the group consisting of hyperlipemia, dyslipidemia, arterial sclerosis, diabetes mellitus, diabetic complications, inflammation, non-alcoholic steatohepatitis, primary biliary circulation and heart disease.

3. The method according to claim 1, wherein the medicament comprising pemafibrate, a salt thereof, or a solvate thereof is a medicament comprising pemafibrate.

4. The method according to claim 1, comprising administering the medicament as 0.1 mg to 0.2 mg of pemafibrate per day to a mild liver cirrhosis patient.

5. The method according to claim 1, comprising administering the medicament as 0.05 mg of pemafibrate twice per day a mild liver cirrhosis patient.

6. The method according to claim 1, comprising administering the medicament as 0.05 mg to 0.1 mg of pemafibrate per day to a moderate liver cirrhosis patient.

7. The method according to claim 1, comprising administering the medicament as 0.025 mg of pemafibrate twice per day to a moderate liver cirrhosis patient.

8. The method according to claim 1, comprising administering the medicament as 0.05 mg of pemafibrate twice per day to a moderate liver cirrhosis patient.

* * * * *